United States Patent
Hagihara et al.

(10) Patent No.: US 8,816,092 B2
(45) Date of Patent: Aug. 26, 2014

(54) INDAZOLE DERIVATIVE OR SALT THEREOF AND PRODUCTION INTERMEDIATE THEREOF, AND ANTIOXIDANT USING SAME, AND USE OF INDAZOLE DERIVATIVE OR SALT THEREOF

(75) Inventors: Masahiko Hagihara, Ube (JP); Ken-ichi Komori, Ube (JP); Hidetoshi Sunamoto, Ube (JP); Hiroshi Nishida, Ube (JP); Yasunori Tsuzaki, Ube (JP); Akira Takama, Ube (JP); Kazutaka Kido, Osaka (JP); Tomokazu Fujimoto, Osaka (JP); Takeshi Matsugi, Osaka (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 13/699,410

(22) PCT Filed: May 26, 2011

(86) PCT No.: PCT/JP2011/062071
§ 371 (c)(1),
(2), (4) Date: Jan. 4, 2013

(87) PCT Pub. No.: WO2011/149011
PCT Pub. Date: Dec. 1, 2011

(65) Prior Publication Data
US 2013/0102787 A1    Apr. 25, 2013

(30) Foreign Application Priority Data

May 27, 2010  (JP) ................... 2010-121822

(51) Int. Cl.
| | |
|---|---|
| *A61K 31/44* | (2006.01) |
| *C07D 401/00* | (2006.01) |
| *C07D 401/14* | (2006.01) |
| *C07D 401/10* | (2006.01) |
| *C07D 405/14* | (2006.01) |
| *C07D 401/04* | (2006.01) |

(52) U.S. Cl.
CPC ........... *C07D 401/14* (2013.01); *C07D 401/10* (2013.01); *C07D 405/14* (2013.01); *C07D 401/04* (2013.01)
USPC ...................................... 546/275.7; 514/338

(58) Field of Classification Search
None
See application file for complete search history.

(56) References Cited

U.S. PATENT DOCUMENTS

| | | |
|---|---|---|
| 2004/0132794 A1 | 7/2004 | Lesuisse et al. |
| 2004/0167127 A1 | 8/2004 | Steffan et al. |
| 2007/0129404 A1 | 6/2007 | Hagihara et al. |
| 2009/0012123 A1 | 1/2009 | Seike et al. |
| 2009/0264468 A1 | 10/2009 | Hagihara et al. |
| 2010/0292207 A1 | 11/2010 | Lombardi Borgia et al. |

FOREIGN PATENT DOCUMENTS

| | | |
|---|---|---|
| CN | 1863779 A | 11/2006 |
| CN | 101160128 A | 4/2008 |
| EP | 1 679 308 A1 | 7/2006 |
| EP | 1 870 099 A1 | 12/2007 |
| JP | 2006-505544 A | 2/2006 |
| RU | 2339624 C2 | 1/2006 |
| WO | WO-2004/031159 A1 | 4/2004 |
| WO | WO 2005/035506 A1 | 4/2005 |
| WO | WO 2006/112313 A1 | 10/2006 |
| WO | WO 2009/013126 A1 | 1/2009 |

OTHER PUBLICATIONS

International Search Report PCT/JP2011/062071 dated Jun. 21, 2011.
Tamio Teramoto et al., "Kekkan Naihi Shogai to Shinkekkanbyo", Biomedicine and Therapeutics, Aug. 2004, vol. 38, No. 8, p. 69.
Chinese Office Action for Application No. 201180025080.0 dated Aug. 14, 2013.
Duo-jiao et al. "Anti-atherogenic effects and mechanism of fasudil on ApoE-/- mice," Journal of Shanghai Jiaotong University (Medical Science), vol. 29, No. 9, Sep. 2009, pp. 1026-1029 and 1048.
Jin et al., "Activation of Rho/Rho kinase signaling pathway by reactive oxygen species in rat aorta," Am J Physiol Heart Circ Physiol, vol. 287, 2004, pp. H1495-H1500.
Tamio Teramoto et al., "Kekkan Naihi Shogai to Shinkekkanbyo", Biomedicine & Therapeutics, Aug. 2004, vol. 38, No. 8, pp. 69-80.
Office Action (Notice of Allowance) dated Jan. 20, 2014 received in Russian Application No. 2012157189.
Chiba et al., "Activation of Rho Is Involved in the Mechanism of Hydrogen-Peroxide-Induced Lung Edema in Isolated Perfused Rabbit Lung," Microvascular Research, vol. 62, 2001, pp. 164-171.

(Continued)

*Primary Examiner* — Heidi Reese
(74) *Attorney, Agent, or Firm* — Foley & Lardner LLP

(57) ABSTRACT

A compound represented by formula (1) or salt thereof and a production intermediate thereof are created. The compound exhibited an excellent antioxidation action in a microsome lipid peroxidation measuring system using a rat liver microsome. Therefore, the compound or salt thereof is useful as an antioxidant. The present invention also provides use of a compound represented by the formula (1) or a pharmaceutically acceptable salt thereof for production of an antioxidant.

(1)

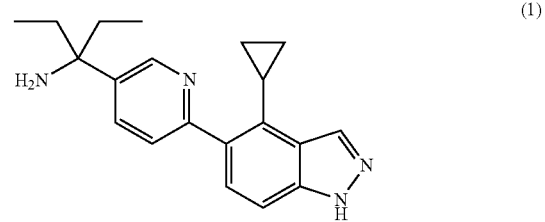

4 Claims, No Drawings

(56) References Cited

OTHER PUBLICATIONS

European Communication for Application No. 11786710.1-1464/ 2578219 PCT/JP2011062071 dated Oct. 16, 2013 with attached Supplementary European Search Report for Application No. EP 11 78 6710 dated Sep. 19, 2013.

Kojima et al., "Direct effects of hydrogen peroxide on airway smooth muscle tone: Roles of $Ca^{2+}$ influx and Rho-kinase," European Journal of Pharmacology, vol. 556, 2007, pp. 151-156.

INDAZOLE DERIVATIVE OR SALT THEREOF AND PRODUCTION INTERMEDIATE THEREOF, AND ANTIOXIDANT USING SAME, AND USE OF INDAZOLE DERIVATIVE OR SALT THEREOF

TECHNICAL FIELD

The present invention relates to a novel indazole derivative or salt thereof, and a production intermediate thereof. The present invention also relates to an antioxidant containing at least one of the indazole derivative or salt thereof as an active ingredient. Further, the present invention relates to use of such an indazole derivative or salt thereof, for production of an antioxidant.

BACKGROUND ART

Recently, it has been revealed that generation of lipid peroxide in a biological body and radical reaction accompanying the same cause various adverse affects on the biological body through a membrane disorder, cell disorder or the like. In association with this, various attempts of application of an antioxidant or a lipid peroxide generation suppressing agent to a medicine have been made, and many studies for antioxidants are made.

For example, as representative antioxidants, vitamin C, vitamin E, polyphenol and the like are used in foods and cosmetics. Also SOD (superoxide dismutase) or the like being an enzyme that brings active oxygen into an oxygen molecule and a hydrogen peroxide molecule is well known as an antioxidant. Further, edaravone is used as a therapeutic agent for preventing enlargement of an infarction site after cerebral infarction by its antioxidation action, and probucol or the like which is a therapeutic agent for hyperlipidemia is known to suppress oxidation of LDL (low density lipoprotein) and have an arteriosclerosis suppressing action. However, not many of these are practically satisfactory because of their weak actions, side effects and the like.

On the other hand, European Patent Publication No. 1679308 (Patent document 1) describes a group of compounds represented by a general formula involving the compounds represented by the following formula (1). Patent document 1 discloses that such a compound group has a Rho kinase inhibiting action, and is useful as a therapeutic agent for glaucoma and the like. European Patent Publication No. 1870099 (Patent document 2) describes a retinal neuron protective agent containing, as an active ingredient, a group of compounds represented by a general formula involving the compounds represented by the following formula (1).

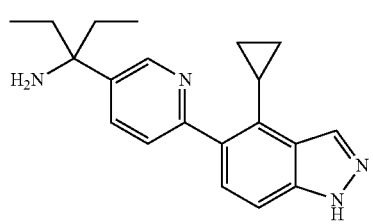

(1)

However, these Patent documents 1, 2 lack disclosure of the compound represented by the above formula (1) itself, and lack description and suggestion for use application of the compound represented by the above formula (1) as an antioxidant.

PRIOR ART DOCUMENTS

Patent Documents

Patent Document 1: European Patent Publication No. 1679308
Patent Document 2: European Patent Publication No. 1870099

SUMMARY OF THE INVENTION

Problems to be Solved by the Invention

It is a very interesting subject to find a novel antioxidant, and to create a novel compound having such an action and effect, or salt thereof, and a production intermediate of such a novel compound.

Means for Solving the Problems

The present inventors made diligent efforts for finding a novel antioxidant, and, as a result, succeeded in creating a novel indazole derivative represented by the formula (1) or salt thereof and found that such a novel compound has an excellent antioxidation action in a microsome lipid peroxidation measuring system using a rat liver microsome. Specifically, the present invention is as follows.

The present invention is an antioxidant containing at least one of a compound represented by the following formula (1) or salt thereof as an active ingredient. Hereinafter, a compound represented by the following formula (1) or salt thereof is called "Inventive compound (1)".

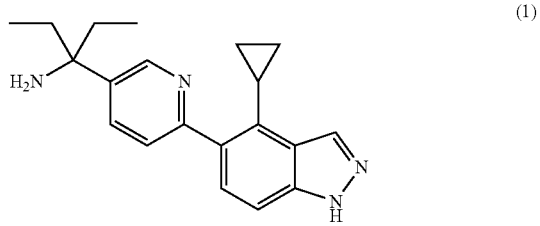 [SMILES: CCC(N)(CC)c1ccc(-c2ccc3[nH]ncc3c2C2CC2)nc1]

(1)

The present invention also provides Inventive compound (1) itself.

The present invention also provides a compound represented by the following formula (2) or salt thereof. Hereinafter, a compound represented by the following formula (2) which is a production intermediate of Inventive compound (1) or salt thereof is called "Inventive compound (2)", and Inventive compound (1) and Inventive compound (2) are generically called "inventive compound".

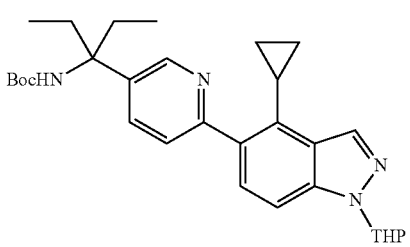

(2)

(wherein, Boc represents a tert-butoxycarbonyl group, and THP represents a tetrahydropyranyl group.)

The present invention also provides use of at least one of a compound represented by the formula (1) or a pharmaceutically acceptable salt thereof for producing an antioxidant.

Effects of the Invention

Inventive compound (1) exhibited an excellent antioxidation action in a microsome lipid peroxidation measuring system using a rat liver microsome. That is, Inventive compound (1) is useful as an antioxidant. Also provided is use of at least one of a compound represented by the formula (1) or a pharmaceutically acceptable salt thereof for producing an antioxidant

MODES FOR CARRYING OUT THE INVENTION

Inventive compound (1) is 1-[6-(4-cyclopropyl-1H-indazol-5-yl)pyridin-3-yl]-1-ethylpropylamine which is an indazole derivative represented by the following formula (1) and salt thereof, and Inventive compound (2) is 1-{6-[4-cyclopropyl-1-(tetrahydropyran-2-yl)-1H-indazol-5-yl]pyridin-3-yl}-1-ethylpropylcarbamic acid tert-butyl ester which is a production intermediate of Inventive compound (1) represented by the following formula (2) and salt thereof.

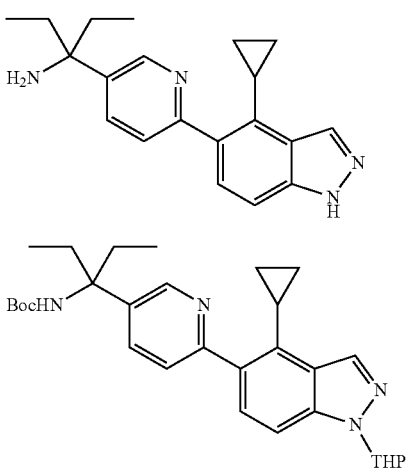

The "salt" in the inventive compound is preferably a pharmaceutically acceptable salt, and for example, salts with inorganic acids such as hydrochloric acid, hydrobromic acid, hydroiodic acid, nitric acid, sulfuric acid, or phosphoric acid, salts with organic acids such as acetic acid, trifluoroacetic acid, oxalic acid, malonic acid, fumaric acid, maleic acid, succinic acid, citric acid, tartaric acid (D-isomer, L-isomer, meso compound), adipic acid, gluconic acid, glucoheptonic acid, glucuronic acid, benzoic acid, phthalic acid, terephthalic acid, lactic acid, hippuric acid, glutamic acid, aspartic acid, 1,2-ethane disulfonic acid, isethionic acid, lactobionic acid, oleic acid, pamoic acid, polygalacturonic acid, stearic acid, tannic acid, methanesulfonic acid, ethanesulfonic acid, trifluoromethanesulfonic acid, benzenesulfonic acid, p-toluenesulfonic acid, lauryl sulfate ester, methyl sulfate, naphthalenesulfonic acid, or sulfosalicylic acid, salts with alkaline metals such as lithium or potassium, salts with alkaline earth metals such as calcium or magnesium, and salts with a quaternary ammonium such as ammonia are recited. Preferably, salts with hydrochloric acid, hydrobromic acid, nitric acid, sulfuric acid, phosphoric acid, fumaric acid, maleic acid, succinic acid, citric acid, tartaric acid (D-isomer, L-isomer, meso-compound) or methanesulfonic acid are recited, and particularly preferably, hydrochloric acid, hydrobromic acid, sulfuric acid, phosphoric acid, fumaric acid, maleic acid, succinic acid, tartaric acid (L-isomer) and methanesulfonic acid are recited. Inventive compound (1) may form a salt at an arbitrary ratio with an inorganic acid, an organic acid, an alkaline metal, an alkaline earth metal or the like, and each of such a salt or a mixture thereof is involved in the present invention.

When there is a hydrate and/or a solvate of the inventive compound, such a hydrate and/or solvate are also involved in the scope of the inventive compound.

When there is a crystalline polymorphism and a crystalline polymorphism group (crystalline polymorphism system) of the inventive compound, such a crystalline polymorphism and a crystalline polymorphism group (crystalline polymorphism system) are also involved in the scope of the inventive compound. Here, the crystalline polymorphism group (crystalline polymorphism system) means crystalline forms in respective stages and the entire course when the crystalline forms variously change with the condition and state of production, crystallization, storage and the like of such crystals (here, the state includes a formulated state).

Preferred concrete examples of the inventive compound can include the following compounds and their salts.

1-[6-(4-cyclopropyl-1H-indazol-5-yl)pyridin-3-yl]-1-ethylpropylamine,

1-[6-(4-cyclopropyl-1H-indazol-5-yl)pyridin-3-yl]-1-ethylpropylamine hydrochloride (hereinafter also referred to as "Compound A"), 1-[6-(4-cyclopropyl-1H-indazol-5-yl)pyridin-3-yl]-1-ethylpropylamine hydrobromide, 1-[6-(4-cyclopropyl-1H-indazol-5-yl)pyridin-3-yl]-1-ethylpropyl amine sulfate, 1-[6-(4-cyclopropyl-1H-indazol-5-yl)pyridin-3-yl]-1-ethylpropylamine phosphate, 1-[6-(4-cyclopropyl-1H-indazol-5-yl)pyridin-3-yl]-1-ethylpropylamine fumarate, 1-[6-(4-cyclopropyl-1H-indazol-5-yl)pyridin-3-yl]-1-ethylpropylamine maleate, 1-[6-(4-cyclopropyl-1H-indazol-5-yl)pyridin-3-yl]-1-ethylpropylamine succinate, 1-[6-(4-cyclopropyl-1H-indazol-5-yl)pyridin-3-yl]-1-ethylpropylamine L-tartrate, 1-[6-(4-cyclopropyl-1H-indazol-5-yl)pyridin-3-yl]-1-ethylpropylamine methanesulfonate, 1-{6-[4-cyclopropyl-1-(tetrahydropyran-2-yl)-1H-indazol-5-yl]pyridin-3-yl}-1-ethylpropylcarbamic acid tert-butyl ester More preferred concrete examples of the inventive compound can include the following compounds and their salts.

1-[6-(4-cyclopropyl-1H-indazol-5-yl)pyridin-3-yl]-1-ethyl-propylamine,
1-[6-(4-cyclopropyl-1H-indazol-5-yl)pyridin-3-yl]-1-ethyl-propylamine 1 hydrochloride,
1-[6-(4-cyclopropyl-1H-indazol-5-yl)pyridin-3-yl]-1-ethyl-propylamine 2 hydrochloride,
1-[6-(4-cyclopropyl-1H-indazol-5-yl)pyridin-3-yl]-1-ethyl-propylamine 3 hydrochloride,
1-[6-(4-cyclopropyl-1H-indazol-5-yl)pyridin-3-yl]-1-ethyl-propylamine 1 hydrobromide,
1-[6-(4-cyclopropyl-1H-indazol-5-yl)pyridin-3-yl]-1-ethyl-propylamine 2 hydrobromide,
1-[6-(4-cyclopropyl-1H-indazol-5-yl)pyridin-3-yl]-1-ethyl-propylamine 3 hydrobromide,
1-[6-(4-cyclopropyl-1H-indazol-5-yl)pyridin-3-yl]-1-ethyl-propylamine 1 sulfate,
1-[6-(4-cyclopropyl-1H-indazol-5-yl)pyridin-3-yl]-1-ethyl-propylamine 1 phosphate,
1-[6-(4-cyclopropyl-1H-indazol-5-yl)pyridin-3-yl]-1-ethyl-propylamine 0.5 fumarate,
1-[6-(4-cyclopropyl-1H-indazol-5-yl)pyridin-3-yl]-1-ethyl-propylamine 1 fumarate,
1-[6-(4-cyclopropyl-1H-indazol-5-yl)pyridin-3-yl]-1-ethyl-propyl amine 1.5 fumarate,
1-[6-(4-cyclopropyl-1H-indazol-5-yl)pyridin-3-yl]-1-ethyl-propylamine 0.5 maleate,
1-[6-(4-cyclopropyl-1H-indazol-5-yl)pyridin-3-yl]-1-ethyl-propylamine 1 maleate,
1-[6-(4-cyclopropyl-1H-indazol-5-yl)pyridin-3-yl]-1-ethyl-propylamine 1.5 maleate,
1-[6-(4-cyclopropyl-1H-indazol-5-yl)pyridin-3-yl]-1-ethyl-propylamine 0.5 succinate,
1-[6-(4-cyclopropyl-1H-indazol-5-yl)pyridin-3-yl]-1-ethyl-propylamine 1 succinate,
1-[6-(4-cyclopropyl-1H-indazol-5-yl)pyridin-3-yl]-1-ethyl-propylamine 1.5 succinate,
1-[6-(4-cyclopropyl-1H-indazol-5-yl)pyridin-3-yl]-1-ethyl-propylamine 0.5 L-tartrate,
1-[6-(4-cyclopropyl-1H-indazol-5-yl)pyridin-3-yl]-1-ethyl-propylamine 1 L-tartrate,
1-[6-(4-cyclopropyl-1H-indazol-5-yl)pyridin-3-yl]-1-ethyl-propylamine 1.5 L-tartrate,
1-[6-(4-cyclopropyl-1H-indazol-5-yl)pyridin-3-yl]-1-ethyl-propylamine 1 methanesulfonate,
1-[6-(4-cyclopropyl-1H-indazol-5-yl)pyridin-3-yl]-1-ethyl-propylamine 2 methanesulfonate,
1-[6-(4-cyclopropyl-1H-indazol-5-yl)pyridin-3-yl]-1-ethyl-propylamine 3 methanesulfonate,
1-{6-[4-cyclopropyl-1-(tetrahydropyran-2-yl)-1H-indazol-5-yl]pyridin-3-yl}-1-ethylpropylcarbamic acid tert-butyl ester While a concrete production method of the inventive compound will be described in detail in the item of Example [Production example] below, as a representative production method, after producing Inventive compound (2) according to the method described in WO2007/142323, the compound is deprotected by a generally used way and/or made into a salt simultaneously and/or subsequently to the deprotection, to produce Inventive compound (1).

While the details will be described in the later-described item of "pharmacological test", Inventive compound (1) exhibited an excellent antioxidation action in a microsome lipid peroxidation measuring system using a rat liver microsome. In other words, Inventive compound (1) is useful as an antioxidant. According to the present invention, also provided is use of the compound represented by the formula (1) or a salt thereof for production of an antioxidant.

Use applications of the antioxidant of the present invention include not only medicines but also cosmetics, foods, industrial products (such as paints) and so on. It is useful preferably as medicines, more preferably as medicines useful for prophylaxis or therapy of a disease for which an antioxidant is considered to be effective, particularly preferably as medicines useful for prophylaxis or therapy of cardiovascular diseases such as arteriosclerosis, atherosclerosis, myocardial infarction, arrhythmia, chronic renal failure, nephritis, hypertension and hyperlipidemia; cranial nervous system diseases such as intracranial hemorrhage, cerebral infarction, subarachnoid hemorrhage, ischemic reperfusion injury, Alzheimer's disease, Parkinson's disease and dementia; digestive system diseases such as gastric ulcer, inflammatory bowel disease, reflux esophagitis, ulcerative colitis, Crohn's disease, diabetes, pancreatitis, hepatitis, hepatic cirrhosis and non-alcoholic steatohepatitis; respiratory system diseases such as pneumonia, emphysema, pulmonary fibrosis, chronic obstructive pulmonary disease and asthma; inflammation/autoimmune diseases such as collagen disease, rheumatism, Behcet's disease and sepsis; skin diseases such as atopic dermatitis, skin inflammation, psoriasis and burn; infections such as herpes infection and AIDS; cancers; anticancer therapies such as adriamycin-induced cardiac toxicity; ophthalmic inflammatory diseases such as corneal inflammation, conjunctivitis, scleritis and blepharitis; dry eye; pterygium; cataract; oxidation stressful eye diseases such as visual fatigue; retinal diseases such as age-related macular degeneration, age-related macular edema (dry type, wet type) and diabetic retinopathy; and glaucoma.

The antioxidant of the present invention may be formulated into a single formulation and/or a mixed formulation using a generally used technique while other active ingredient and/or additive (preferably, other pharmaceutically acceptable active ingredient and/or additive) is added as necessary.

The antioxidant of the present invention may be orally or parenterally administered to a patient when it is applied for prophylaxis or therapy of a disease for which an antioxidant is considered to be effective, and as an administration form, oral administration, topical administration to eye (e.g., eye drop administration, administration into conjunctival sac, intravitreal administration, subconjunctival administration, and subtenon administration), intravenous administration, transdermal administration and the like are recited, and the antioxidant is formulated into a dosage form suited for administration together with a pharmaceutically acceptable additive as necessary. As a dosage form suited for oral administration, for example, a tablet, a capsule, a granule, a fine granule, a powder and the like are recited, and as a dosage form suited for parenteral administration, for example, an injection, an eye drop, an eye ointment, a patch, gel, an intercalating agent and the like are recited. These may be prepared by using ordinary techniques that are generally used in this field of art. The antioxidant of the present invention may also be prepared into a formulation employing DDS (drug delivery system) such as a formulation for intraocular implant and microsphere besides the above formulations.

For example, a tablet may be prepared by appropriately selecting and using an excipient such as lactose, glucose, D-mannitol, anhydrous calcium hydrogenphosphate, starch or sucrose; a disintegrant such as carboxymethyl cellulose, carboxymethyl cellulose calcium, croscarmellose sodium, crospobidone, starch, partially-gelatinized starch, or low-substituted hydroxypropyl cellulose; a binder such as hydroxypropyl cellulose, ethyl cellulose, gum arabic, starch, partially-gelatinized starch, polyvinylpyrrolidone, or polyvinyl alcohol; a lubricant such as magnesium stearate, calcium stearate, talc, hydrous silicon dioxide, or hardened oil; a coating agent such as purified saccharose, hydroxypropylmethyl cellulose, hydroxypropyl cellulose, methyl cellulose, or pyrrolidone; and a corrigent such as citric acid, Aspartame, ascorbic acid, or menthol.

An injection may be prepared while selecting and using as necessary, an isotonizing agent such as sodium chloride; a buffer such as sodium phosphate; a surfactant such as polyoxyethylene sorbitan monooleate; a thickener such as methylcellulose and so on.

An eye drop may be prepared while selecting and using as necessary, an isotonizing agent such as sodium chloride or concentrated glycerin; a buffer such as sodium phosphate or sodium acetate; a surfactant such as polyoxyethylene sorbitan monooleate, polyoxyl stearate 40, or polyoxyethylene hardened castor oil; a stabilizer such as sodium citrate or sodium edetate; and a preservative such as benzalkonium chloride or paraben, and pH may be within a range accepted for ophthalmic formulation, and usually preferably within a range of 4 to 8. Also, an eye ointment may be prepared by using a generally used base such as white petrolatum or liquid paraffin.

An intercalating agent may be prepared by grinding and mixing a biodegradable polymer such as hydroxypropyl cellulose, hydroxypropylmethyl cellulose, carboxyvinyl polymer or polyacrylic acid together with an active ingredient, followed by compression molding of the resultant powder, and an excipient, a binder, a stabilizer, and a pH modifier may be used as necessary.

A formulation for intraocular implant may be prepared by using a biodegradable polymer, for example, a biodegradable polymer such as polylactic acid, polyglycolic acid, lactic acid-glycolic acid copolymer, or hydroxypropyl cellulose.

A dose of the antioxidant of the present invention may be varied appropriately depending on the dosage form, severity of condition, age, body weight of the patient to which the agent is administered, decision by a physician and so on, however, in the case of oral administration, generally, 0.01 to 5000 mg, preferably 0.1 to 2500 mg, and more preferably 0.5 to 1000 mg may be administered per a day to an adult in a single dose or in several batches. In the case of an injection, generally, 0.0001 to 2000 mg may be administered to an adult in a single dosage or in several batches. Further, in the case of an eye drop or an intercalating agent, one having an active ingredient concentration of 0.000001 to 10% (w/v), preferably 0.00001 to 1% (w/v), more preferably 0.0001 to 0.1% (w/v) may be administered once or several times a day. In the case of a patch, a patch containing 0.0001 to 2000 mg may be affixed to an adult, and in the case of a formulation for intraocular implant, a formulation for intraocular implant containing 0.0001 to 2000 mg for an adult may be implanted in an eye.

The production examples, pharmacological test examples, and formulation examples shown below are given for better understanding of the present invention, rather than limiting the scope of the present invention.

PRODUCTION EXAMPLES

Example 1

Synthesis of 1-{6-[4-cyclopropyl-1-(tetrahydropyran-2-yl)-1H-indazol-5-yl]pyridin-3-yl}-1-ethylpropylcarbamic acid tert-butyl ester To a solution of 4-cyclopropyl-1-(tetrahydropyran-2-yl)-5-(4,4,5,5-tetramethyl[1,3,2]dioxaboranyl)-1H-indazole (130 g, 353 mmol, see WO2007/142323) in toluene (720 g) were added ethanol (140 mL), water (140 mL), potassium phosphate dihydrate (230 g, 933 mmol) and 2-bromo-5-(1-tert-butoxycarbonylamino-1-ethylpropyl)pyridine (100 g, 291 mmol, see WO2005/035506) under an argon gas flow. The reaction solution was aerated for 10 minutes with argon gas. Then, under an argon gas flow, a 20 wt. % tricyclohexylphosphine/toluene solution (10 mL, 6.22 mmol) and palladium acetate (700 mg, 3.11 mmol) were added, and heated and stirred at 75° C. for 6 hours.

After end of the reaction, to the reaction solution was added water (200 mL) and separated. The organic layer was washed with saturated saline (300 mL) and caused to pass through Celite (trade name) (20 g), and then concentrated under reduced pressure. To the obtained residue was added heptane (1000 mL), and the generated solid was collected by filtration and washed with heptane. The obtained solid was dried under reduced pressure at 48° C., to obtain 1-{6-[4-cyclopropyl-1-(tetrahydropyran-2-yl)-1H-indazol-5-yl]pyridin-3-yl}-1-ethylpropylcarbamic acid tert-butyl ester (Example compound 1) (104 g) represented by the following formula as a white powder (yield 66%).

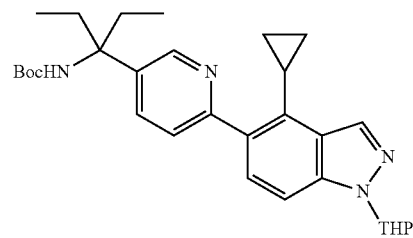

Mass spectrum (CI, m/z): 505 ([M+H]$^+$)
$^1$H-NMR spectrum (CDCl$_3$): δ 0.50-0.55 (m, 2H), 0.75-0.87 (m, 8H), 1.40 (brs, 9H), 1.63-2.37 (m, 10H), 2.53-2.66 (m, 1H), 3.71-3.79 (m, 1H), 4.01-4.07 (m, 1H), 4.81 (brs, 1H), 5.72 (dd, J=9.3, 2, 7, 1H), 7.47-7.59 (m, 3H), 7.68 (dd, J=8.2, 2.4 Hz, 1H), 8.21 (s, 1H), 8.69 (dd, J=2.4, 0.7 Hz, 1H).

Example 2

Synthesis of 1-[6-(4-cyclopropyl-1H-indazol-5-yl)pyridin-3-yl]-1-ethylpropylamine hydrochloride To 1-{6-[4-cyclopropyl-1-(tetrahydropyran-2-yl)-1H-indazol-5-yl]pyridin-3-yl}-1-ethylpropylcarbamic acid tert-butyl ester (Example compound 1, 100 g, 198 mmol) were added ethanol (250 mL), water (11 mL) and a 38 wt. % hydrogen chloride/ethanol solution (179 mL), and stirred at a temperature of 30° C. to 43° C. for 5 hours under an argon gas flow.

The reaction solution was cooled to 12° C., and stirred for 0.3 hours at the same temperature. The precipitated solid was collected by filtration, and then washed with ethanol (100 mL). To the obtained solid (90 g) was added ethanol (270 mL), and heated to 75° C. Then water (35 mL) was added and heated and stirred for 0.5 hours. The reaction was cooled to 10° C., and the generated solid was collected by filtration, and washed with ethanol (200 mL), and then dried at 40° C. for 10 hours, to obtain a white solid (71 g).

To the obtained solid (70 g) was added a mixed solution (234 mL) of ethanol/water 2/1 (v/v), and heated and stirred at a temperature of 70° C. to 75° C. for 0.5 hours under an argon gas flow. The reaction was cooled to 10° C., and the precipitated solid was collected by filtration, and washed with 90 mL of ethanol. By drying at 50° C. for 2 hours, 1-[6-(4-cyclopropyl-1H-indazol-5-yl)pyridin-3-yl]-1-ethylpropylamine hydrochloride (Example compound 2) (46 g) was obtained as a white powder (yield 62%).

Melting point: >250° C. (degradation).
Mass spectrum (CI, m/z): 321 ([M+H]$^+$)
$^1$H-NMR spectrum (CD$_3$OD): δ 0.44-0.50 (m, 2H), 0.97-1.04 (m, 8H), 2.16-2.54 (m, 5H), 7.58-7.69 (m, 2H), 8.38-8.41 (m, 2H), 8.73 (dd, J=8.5, 2.4 Hz, 1H), 9.02 (dd, J=2.4, 0.5 Hz, 1H).

Example 3

Synthesis of 1-[6-(4-cyclopropyl-1H-indazol-5-yl)pyridin-3-yl]-1-ethylpropylamine hydrobromide To 1-{6-[4-cyclopropyl-1-(tetrahydropyran-2-yl)-1H-indazol-5-yl]pyridin-3-yl}-1-ethylpropylcarbamic acid tert-butyl ester (Example compound 1, 2.1 g, 4.2 mmol) were added ethanol (20 mL) and a 48 wt. % hydrogen bromide solution (10 mL), and heated and stirred for 4 hours at 40° C. The solvent was distilled off under reduced pressure, and to the residue was added at 50° C. ethanol (10 mL) and water (2 mL). After cooling on ice water, the precipitated solid was collected by filtration and washed with ethanol, to obtain a white solid (883 mg).

To the obtained white solid (530 mg) were added ethanol (5 mL) and water (200 μL), and heated and stirred at 70° C. for 0.5 hours. After cooling to room temperature, the precipitated solid was collected by filtration, and washed with ethanol, and then dried at 60° C. for 1.25 hours, to obtain 1-[6-(4-cyclopropyl-1H-indazol-5-yl)pyridin-3-yl]-1-ethylpropylamine hydrobromide (Example compound 3) (273 mg) as a white powder (yield 22%).

Melting point: >221-223° C. (degradation)
Mass spectrum (CI, m/z): 321 ([M+H]$^+$)
$^1$H-NMR spectrum (CD$_3$OD): δ 0.45-0.50 (m, 2H), 0.97-1.04 (m, 8H), 2.17-2.53 (m, 5H), 7.60 (d, J=8.8 Hz, 1H), 7.65-7.69 (m, 1H), 8.39-8.42 (m, 2H), 8.72 (dd, J=8.8, 2.4 Hz, 1H), 9.02 (dd, J=2.4, 0.5 Hz, 1H).

Example 4

Synthesis of 1-[6-(4-cyclopropyl-1H-indazol-5-yl)pyridin-3-yl]-1-ethylpropylamine To 1-[6-(4-cyclopropyl-4H-indazol-5-yl)pyridin-3-yl]-1-ethylpropylamine hydrochloride (Example compound 2, 30.0 g, 76.3 mmol) were added n-butanol (300 mL) and a 4M aqueous sodium hydroxide solution (370 mL), and stirred at room temperature for 1.5 hours. The organic layer was separated, and washed with water (150 mL), and then the organic layer was concentrated, to obtain a solid (22.6 g).

To the obtained solid (22.6 g) was added methanol (160 mL), and the temperature was raised to 60° C. Water (160 mL) was added at the same temperature, and after stirring for 0.5 hours, stirring was conducted for 1 hour at a temperature of 10° C. to 15° C. After filtering the reaction solution, the obtained solid was washed with a mixed solution (46 mL) of cold methanol/water=1/1 (v/v). By drying for 11 hours at 80° C. under reduced pressure, 1-[6-(4-cyclopropyl)-1H-indazol-5-yl)pyridin-3-yl]-1-ethylpropylamine (Example compound 4) (21.5 g) represented by the following formula was obtained as a white powder (yield 88%).

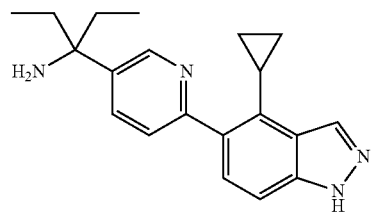 [SMILES: CCC(N)(CC)c1ccc(-c2ccc3[nH]ncc3c2C2CC2)nc1]

Melting point: 208° C.
Mass spectrum (CI, m/z): 321 ([M+H]$^+$)
$^1$H-NMR spectrum (CD$_3$OD): δ 0.41-0.47 (m, 2H), 0.79-0.86 (m, 8H), 1.75-2.04 (m, 4H), 2.28-2.37 (m, 1H), 7.42-7.49 (m, 2H), 7.62 (dd, J=8.3, 0.7 Hz, 1H), 7.93 (dd, J=8.3, 2.4 Hz, 1H), 8.24 (d, J=0.7 Hz, 1H), 8.67 (dd, J=2.4, 0.7 Hz, 1H).

Example 5

Synthesis of 1-[6-(4-cyclopropyl-1H-indazol-5-yl)pyridin-3-yl]-1-ethylpropylamine L-tartrate To a solution of 1-[6-(4-cyclopropyl-1H-indazol-5-yl)pyridin-3-yl]-1-ethylpropylamine (Example compound 4, 4.0 g, 12 mmol) in ethanol (160 mL) was added dropwise a solution of L-tartaric acid (2.8 g, 19 mmol) in ethanol (85 mL) at room temperature over 0.5 hours, and stirred at the same temperature for 0.67 hours. The reaction solution was cooled to 10° C., and the precipitated solid was collected by filtration. After washing with ethanol (40 mL), the solid was dried under reduced pressure at 40° C. for 1 hour, and then the temperature was raised to 60° C. and dried under reduced pressure for 11 hours, to obtain 1-[6-(4-cyclopropyl-1H-indazol-5-yl)pyridin-3-yl]-1-ethylpropylamine L-tartrate (Example compound 5) (5.4 g) as a white solid (yield 92%).

Melting point: 215-216° C.
Mass spectrum (CI, m/z): 321 ([M+14]$^+$)
$^1$H-NMR spectrum (CD$_3$OD): δ 0.41-0.46 (m, 2H), 0.83-0.89 (m, 2H), 0.95 (t, J=7.4 Hz, 6H), 2.10 (dq, J=14.8, 7.4 Hz, 2H), 2.26 (dq, J=14.8, 7.4 Hz, 2H), 2.34-2.42 (m, 1H), 4.40 (s, 2H), 7.46-7.52 (m, 2H), 7.81 (dd, J=8.3, 0.5 Hz, 1H), 7.97 (dd, J=8.3, 2.7 Hz, 1H), 8.27 (d, J=0.7 Hz, 1H), 8.66-8.67 (m, 1H).

Example 6

Synthesis of 1-[6-(4-cyclopropyl-1H-indazol-5-yl)pyridin-3-yl]-1-ethylpropylamine maleate To a solution of maleic acid (11 mg, 0.095 mmol) in tetrahydrofuran (110 μL) was added a solution of 1-[6-(4-cyclopropyl-1H-indazol-5-yl)pyridin-3-yl]-1-ethylpropylamine (Example compound 4, 10 mg, 0.031 mmol) in tetrahydrofuran (800 μL), and left still for 6 days at room temperature. The precipitated solid was collected by filtration, and dried under reduced pressure at 50° C., to obtain 1-[6-(4-cyclopropyl-1H-indazol-5-yl)pyridin-3-yl]-1-ethylpropylamine maleate (Example compound 6) (11 mg) as a white solid (yield 71%).

Melting point: 174-178° C.
$^1$H-NMR spectrum (CD$_3$OD): δ 0.41-0.46 (m, 2H), 0.83-0.90 (m, 2H), 0.96 (t, J=7.5 Hz, 6H), 2.10 (dq, J=14.8, 7.5 Hz, 2H), 2.21-2.42 (m, 3H), 6.27 (s, 3H), 7.46-7.53 (m, 2H), 7.82 (dd, J=8.5, 0.6 Hz, 1H), 7.94 (dd, J=8.5, 2.7 Hz, 1H), 8.27 (s, 1H), 8.65-8.66 (m, 1H).

Example 7

Synthesis of 1-[6-(4-cyclopropyl-1H-indazol-5-yl)pyridin-3-yl]-1-ethylpropylamine fumarate To a solution of fumaric acid (11 mg, 0.095 mmol) in tetrahydrofuran (275 μL) was added a solution of 1-[6-(4-cyclopropyl-1H-indazol-5-yl)pyridin-3-yl]-1-ethylpropylamine (Example compound 4, 10 mg, 0.031 mmol) in tetrahydrofuran (667 μL), and left still for 3 days at room temperature. The precipitated solid was collected by filtration, and dried under reduced pressure at 50° C., to obtain 1-[6-(4-cyclopropyl-1H-indazol-5-yl)pyridin-3-yl]-1-ethylpropylamine fumarate (Example compound 7) (8.8 mg) as a white solid (yield 75%).

Melting point: 257° C.

$^1$H-NMR spectrum (CD$_3$OD): δ 0.41-0.46 (m, 2H), 0.82-0.94 (m, 8H), 1.94-2.07 (m, 2H), 2.18 (dq, J=14.8, 7.3 Hz, 2H), 2.31-2.41 (m, 1H), 6.68 (s, 1H), 7.45-7.51 (m, 2H), 7.76 (dd, J=8.3, 0.7 Hz, 1H), 7.95 (dd, J=8.3, 2.4 Hz, 1H), 8.26 (d, J=0.7 Hz, 1H), 8.66 (dd, J=2.4, 0.7 Hz, 1H).

Example 8

Synthesis of 1-[6-(4-cyclopropyl-1H-indazol-5-yl)pyridin-3-yl]-1-ethylpropylamine succinate To a solution of succinic acid (11 mg, 0.093 mmol) in tetrahydrofuran (275 μL) was added a solution of 1-[6-(4-cyclopropyl-1H-indazol-5-yl)pyridin-3-yl]-1-ethylpropylamine (Example compound 4, 10 mg, 0.031 mmol) in tetrahydrofuran (667 μL), and left still for 6 days at room temperature. The precipitated solid was collected by filtration, and dried under reduced pressure at 50° C., to obtain 1-[6-(4-cyclopropyl-1H-indazol-5-yl)pyridin-3-yl]-1-ethylpropylamine succinate (Example compound 8) (6.9 mg) as a white solid (yield 58%).

Melting point: 218° C.

$^1$H-NMR spectrum (CD$_3$OD): δ 0.41-0.46 (m, 2H), 0.82-0.90 (m, 8H), 1.94 (dq, J=14.6, 7.3 Hz, 2H), 2.11 (dq, J=14.6, 7.3 Hz, 2H), 2.30-2.40 (m, 1H), 2.51 (s, 2H), 7.44-7.51 (m, 2H), 7.72 (d, J=8.3 Hz, 1H), 7.94 (dd, J=8.3, 2.4 Hz, 1H), 8.25 (d, J=0.7 Hz, 1H), 8.66 (d, J=2.4 Hz, 1H).

Pharmacological Test Example

1. Antioxidation Action Test in Rat Liver Microsome

Using a microsome lipid peroxidation measuring system, an antioxidation action of a test compound was evaluated. This test quantifies a thiobarbituric acid reaction substance (TBARS) that is generated by a lipid peroxidation reaction caused by adding nicotinamide adenine dinucleotide phosphoric acid and ferrous sulfate to a microsome. To this system, a test compound is added, and a TBARS generation suppressing action by the test compound is evaluated as an antioxidation action. This method is a general method for measuring an antioxidation action of a compound or the like (Reference document: Yakugaku Zasshi 119, 93-99 (1999), Biochimica et Biophysics Acta, 1046, (1990) 207-213, Chemistry & Biology Experiment line 2, lipid peroxidation experimental method (Hirokawa shoten)).

<Preparation of Reagent for Testing Antioxidation Action, Preparation of Test Compound Solution, and Evaluation Method>

(Preparations of Reagents)

1) Preparation of Buffer Solution

A buffer solution was prepared by mingling to achieve 25 mM tris(hydroxymethyl)aminomethane (Tris) (pH 7.4) and 150 mM potassium chloride (KCl).

2) Preparation of 5 mM Ferrous Sulfate Solution

Ferrous sulfate (FeSO$_4$.7H$_2$O) was dissolved in distilled water to prepare a 5 mM solution.

3) Preparation of 50 mM Nicotinamide Adenine Dinucleotide Phosphoric Acid Solution Nicotinamide adenine dinucleotide phosphoric acid (NADPH) was dissolved in distilled water to prepare a 50 mM solution.

4) Preparation of 200 mM Ethylenediaminetetraacetic Acid Solution

Ethylenediaminetetraacetic acid (EDTA) was dissolved in distilled water to prepare a 200 mM solution.

5) Rat Liver Microsome

Five μL of a commercially available rat liver microsome [XENOTECH, catalog No. R1000 (20 mg protein/mL)] was used.

(Preparation of Test Compound Solution)

As a test compound, Compound A which is an inventive compound [1-[6-(4-cyclopropyl-1H-indazol-5-yl)pyridin-3-yl]-1-ethylenepropylamine hydrochloride (Example compound 2)], and Compound B having a similar compound structure [1-[6-(4-cyclopropyl-1H-indazol-5-yl)pyridin-3-yl]-1-methyl ethyl amine hydrochloride (synthesized according to a method described in European Patent Publication No. 1679308)] were used. Ten mM test compound solutions were prepared by dissolving 1.3 mg of Compound A in 0.315 mL of dimethyl sulfoxide (DMSO), and dissolving 2.15 mg of Compound B in 0.554 mL of dimethyl sulfoxide (DMSO).

Compound A

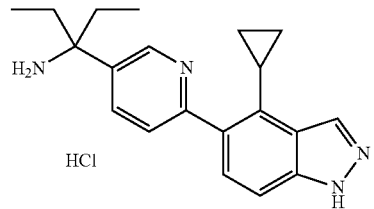

Compound B

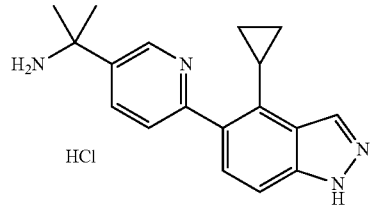

(Evaluation Method)

1) A test compound solution (5 μL) was put into a reaction tube.

2) A buffer solution (480 μL) was put into the reaction tube.

3) Then, to each reaction tube was added 5 μL of a rat liver microsome, mingled, and pre-incubated for 5 minutes in an incubator (37° C.).

4) A 50 mM nicotinamide adenine dinucleotide phosphoric acid solution (5 μL) was added to each reaction tube so that the final concentration was 500 μM.

5) A 5 mM ferrous sulfate solution (5 μL) was added to each reaction tube so that the final concentration was 50 μM, and the reaction was started.

6) Following the reaction for 20 minutes, a 200 mM ethylenediaminetetraacetic acid solution (25 μL) was added to each reaction tube so that the final concentration was 10 mM to stop the reaction, and left still in iced water.

7) A thiobarbituric acid reaction substance (TBARS) generation value in the reaction completed solution was measured using a commercially available TBARS measuring kit [Cayman, Catalog No. 10009055].

As a non-lipid peroxidation reaction group, a test was conducted by adding distilled water in place of nicotinamide adenine dinucleotide phosphoric acid and ferrous sulfate, and a TBARS generation value was measured. The number of examples of each group is n=2, and the TBARS generation suppressing rate (%) was calculated from an average value of n=2 according to the following formula 1, and $IC_{50}$ of the test compound was measured by nonlinear regression of statistical analysis software (EXSAS).

TBARS generation suppressing rate (%)=$[1-(T_x-T_0)/(T_n-T_0)] \times 100$  [Formula 1]

$T_0$: TBARS generation value of non-lipid peroxidation reaction group (μM)
$T_n$: TBARS generation value of control solution added-group (μM)
$T_x$: TBARS generation value of test compound added-group (μM)

(Compound Adding Method)

Test compound added-group: A compound solution dissolved in dimethyl sulfoxide (DMSO) solution was added.

Control solution added-group and Non-lipid peroxidation reaction group: A dimethyl sulfoxide (DMSO) solution was added.

TABLE 1

|  | $IC_{50}$ |
|---|---|
| Compound A | 3.8 μM |
| Compound B | >100 μM |

(Discussion)

From these results, Compound A exhibited a strong antioxidation action. On the other hand, Compound B did not exhibit a strong antioxidation action although having a similar structure to Compound B.

Formulation Examples

The drug of the present invention will be described more specifically by way of formulation examples, however, it is to be noted that the present invention will not be limited only to these formulation examples.

Formulation Example 1

Tablet

In 100 mg,

| Compound A | 1 mg |
|---|---|
| Lactose | 66.4 mg |
| Corn starch | 20 mg |
| Carboxymethylcellulose calcium | 6 mg |
| Hydroxypropylcellulose | 6 mg |
| Magnesium stearate | 0.6 mg |

Compound A and lactose are mixed in a mixing machine, and to the mixture are added carboxymethylcellulose calcium and hydroxypropylcellulose, and granulated, and the obtained granules are particle-size regulated after drying, and to the particle-size regulated granules is added magnesium stearate and mixed, followed by tableting in a tableting machine. Further, by varying the adding amount of Compound A, it is possible to prepare a tablet containing 0.1 mg, 10 mg or 50 mg in 100 mg.

Formulation Example 2

Eye Ointment

In 100 g,

| Compound A | 0.3 g |
|---|---|
| Liquid paraffin | 10.0 g |
| White vaseline | q.s. |

To uniformly molten white vaseline and liquid paraffin is added Compound A, and these are mixed well and then gradually cooled to prepare an eye ointment. By varying the adding amount of Compound A, it is possible to prepare an eye ointment having a concentration of 0.05% (w/w), 0.1% (w/w), 0.5% (w/w) or 1% (w/w).

Formulation Example 3

Injection

In 10 mL,

| Compound A | 10 mg |
|---|---|
| Sodium chloride | 90 mg |
| Polysolvate 80 | q.s. |
| Sterile purified water | q.s. |

Compound A and sodium chloride are added to sterile purified water to prepare an injection. By varying the adding amount of Compound A, it is possible to prepare an injection containing 0.1 mg, 10 mg or 50 mg in 10 mL.

Formulation Example 4

Eye Drop

In 100 mL,

| Compound A | 10 mg |
|---|---|
| Sodium chloride | 900 mg |
| Polysolvate 80 | q.s. |
| Disodium hydrogenphosphate | q.s. |
| Sodium dihydrogenphosphate | q.s. |
| Sterile purified water | q.s. |

To sterile purified water were added Compound A and other ingredients as described above, and these are mixed well to prepare an eye drop. By varying the adding amount of Compound A, it is possible to prepare an eye drop having a concentration of 0.05% (w/v), 0.1% (w/v), 0.5% (w/v) or 1% (w/v).

It is to be understood that the embodiments and examples disclosed herein are given for exemplification and not for limitation in all respects. The scope of the present invention is defined by claims rather than by the above description, and it is intended that any modifications within the meanings of equivalent and the scopes of the claims are included.

INDUSTRIAL APPLICABILITY

Inventive compound (1) exhibited an excellent antioxidation action in a microsome lipid peroxidation measuring system using a rat liver microsome. Therefore, Inventive Compound (1) is useful as an antioxidant.

The invention claimed is:

1. An antioxidant containing at least one of a compound represented by the following formula (1) or salt thereof as an active ingredient:

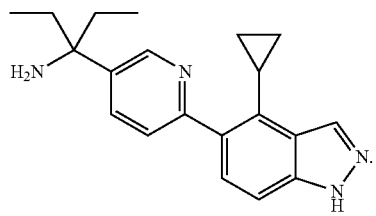
(1)

2. A compound represented by the following formula (1) or salt thereof:

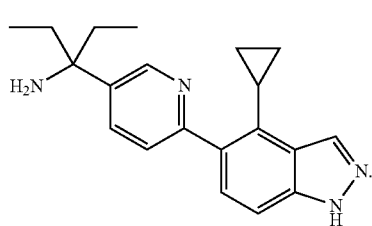
(1)

3. A compound represented by the following formula (2) or salt thereof:

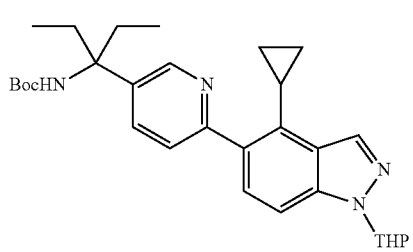
(2)

(wherein Boc represents a tert-butoxycarbonyl group, and THP represents a tetrahydropyranyl group).

4. A pharmaceutical composition which comprises the compound or salt thereof according to claim 2 as an active ingredient.

* * * * *